United States Patent
Glik et al.

(10) Patent No.: US 12,201,364 B2
(45) Date of Patent: Jan. 21, 2025

(54) EYE CUP FOR PASSIVE FEEDBACK FOR FUNDUS CAMERA ALIGNMENT

(71) Applicant: Verily Life Sciences LLC, Dallas, TX (US)

(72) Inventors: Eliezer Glik, San Francisco, CA (US); Sam Kavusi, Menlo Park, CA (US)

(73) Assignee: Verily Life Sciences LLC, Dallas, TX (US)

( * ) Notice: Subject to any disclaimer, the term of this patent is extended or adjusted under 35 U.S.C. 154(b) by 487 days.

(21) Appl. No.: 17/770,858

(22) PCT Filed: Oct. 30, 2020

(86) PCT No.: PCT/US2020/058297
§ 371 (c)(1),
(2) Date: Apr. 21, 2022

(87) PCT Pub. No.: WO2021/133464
PCT Pub. Date: Jul. 1, 2021

(65) Prior Publication Data
US 2022/0361750 A1    Nov. 17, 2022

Related U.S. Application Data

(60) Provisional application No. 62/953,722, filed on Dec. 26, 2019.

(51) Int. Cl.
*A61B 3/15* (2006.01)
*A61B 3/12* (2006.01)

(52) U.S. Cl.
CPC ............. *A61B 3/152* (2013.01); *A61B 3/12* (2013.01)

(58) Field of Classification Search
CPC ............. A61B 3/152; A61B 3/12; A61B 3/14
USPC ........................................................ 351/206
See application file for complete search history.

(56) References Cited

U.S. PATENT DOCUMENTS

| | | | |
|---|---|---|---|
| 6,830,347 B2 | 12/2004 | Slawson et al. |
| 7,854,510 B2 | 12/2010 | Verdooner et al. |
| 8,714,743 B2 | 5/2014 | Verdooner |
| 8,842,981 B2 | 9/2014 | Fujikake et al. |

(Continued)

OTHER PUBLICATIONS

International Search Report and Written Opinion mailed Feb. 12, 2021, in corresponding International Patent Application No. PCT/US2020/058297, 7 pages.

*Primary Examiner* — Tuyen Tra
*Assistant Examiner* — Rahman Abdur
(74) *Attorney, Agent, or Firm* — Christensen O'Connor Johnson Kindness PLLC

(57) ABSTRACT

Eye cups and retinal imaging systems including an eye cup are described. In an embodiment, the eye cup is shaped to couple with an eyepiece lens assembly. In an embodiment, the eye cup includes a concave socket shaped to couple to a periorbital region of an eye, the concave socket defining a viewing aperture positioned to align with a pupil of the eye along a longitudinal axis of the viewing aperture when the concave socket is coupled to the periorbital region; and a flange extending from the concave socket away from the longitudinal axis and shaped to couple with a lateral margin of the periorbital region when the concave socket is coupled to the periorbital region. In an embodiment, an outer edge of the flange extends farther from the longitudinal axis than an outer edge of portion of the concave socket.

20 Claims, 10 Drawing Sheets

(56) References Cited

U.S. PATENT DOCUMENTS

| | | | |
|---|---|---|---|
| 9,146,394 B1* | 9/2015 | Brillhart | H04N 23/63 |
| 9,521,950 B2 | 12/2016 | Verdooner | |
| 10,043,430 B1 | 8/2018 | D'Amico et al. | |
| 10,154,782 B2 | 12/2018 | Farchione et al. | |
| 2007/0206153 A1* | 9/2007 | Siminou | A61B 3/10 |
| | | | 351/245 |
| 2007/0225692 A1* | 9/2007 | Somani | G01J 1/4257 |
| | | | 250/252.1 |
| 2011/0234977 A1* | 9/2011 | Verdooner | A61B 3/135 |
| | | | 351/207 |
| 2016/0205298 A1 | 7/2016 | Zhou | |

* cited by examiner

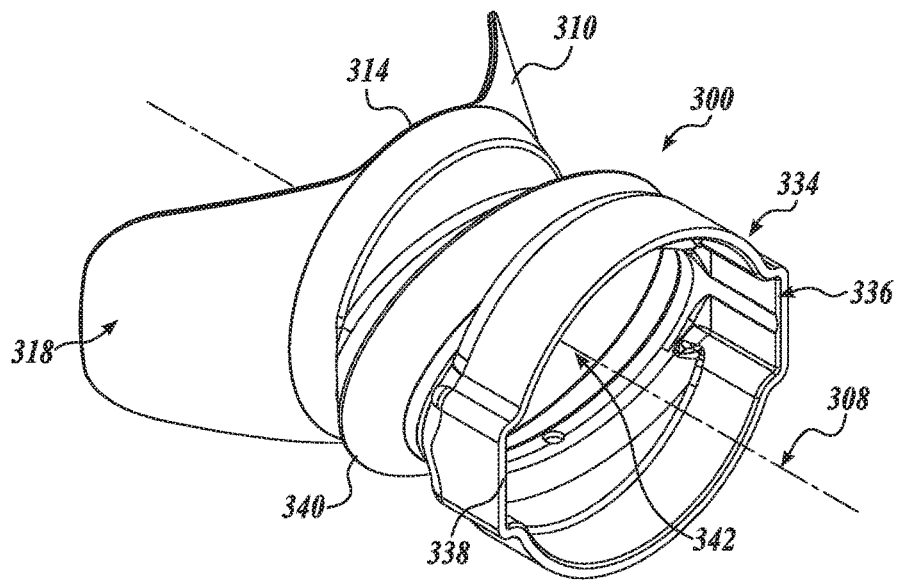
FIG. 3A
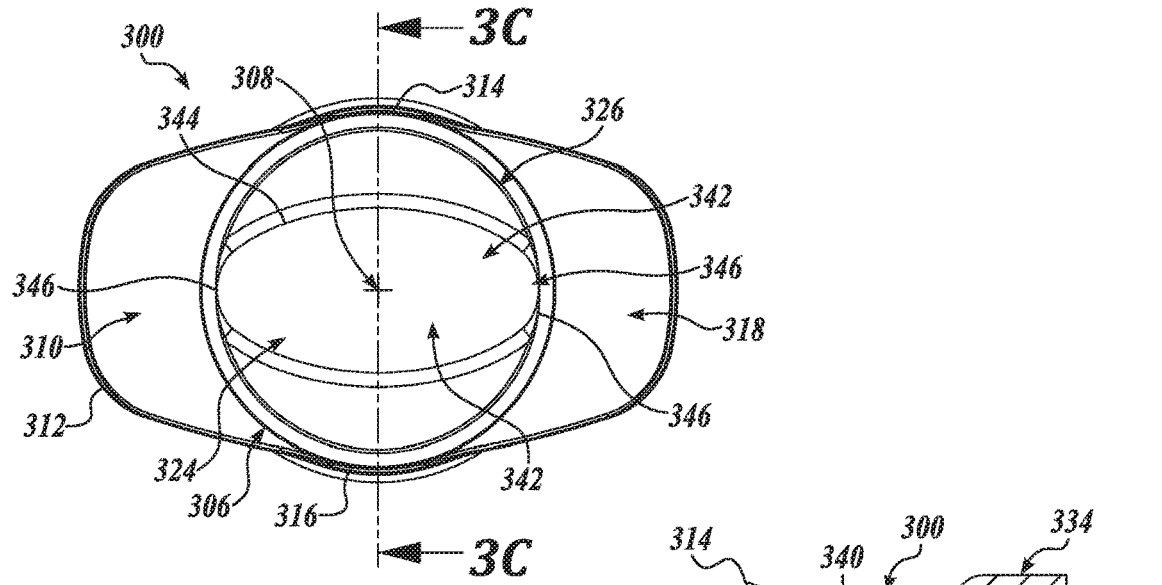
FIG. 3B
FIG. 3C

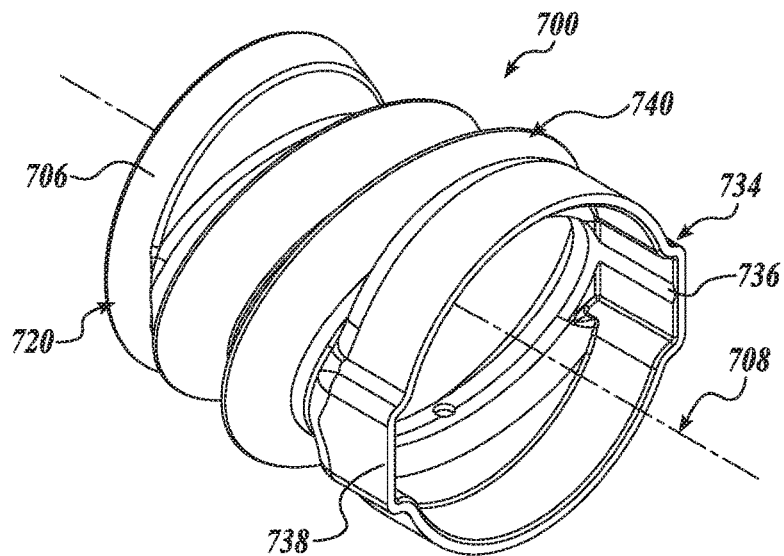
FIG. 7A
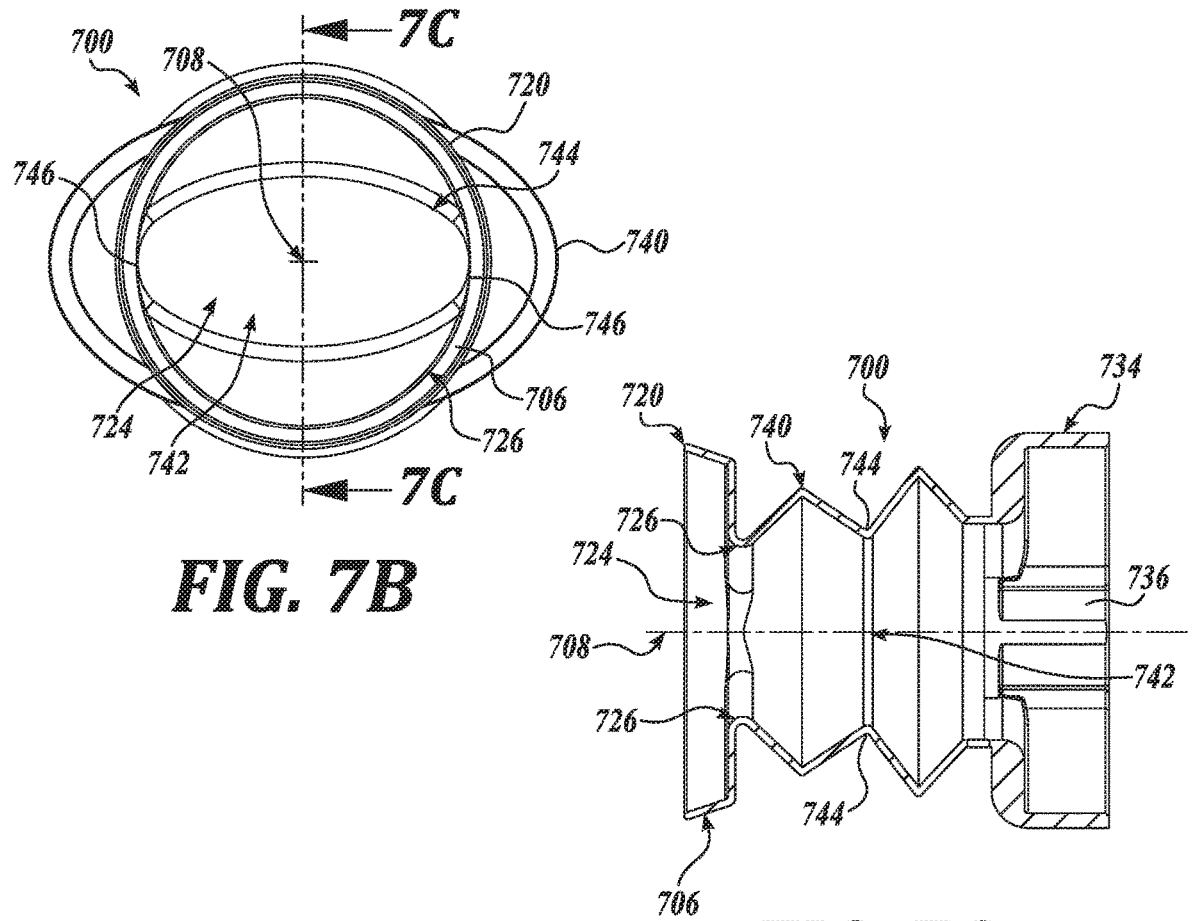
FIG. 7B
FIG. 7C

EYE CUP FOR PASSIVE FEEDBACK FOR FUNDUS CAMERA ALIGNMENT

CROSS-REFERENCE TO RELATED APPLICATIONS

This application is a 371 National Stage of International Application No. PCT/US2020/058297 filed on Oct. 30, 2020, which claims priority to U.S. Provisional Application No. 62/953,722, filed on Dec. 26, 2019, which is hereby incorporated by reference in its entirety.

TECHNICAL FIELD

This disclosure relates generally to eye cups, and in particular but not exclusively, relates to eye cups for a fundus camera.

BACKGROUND INFORMATION

Retinal imaging is a part of basic eye exams for screening, field diagnosis, and progress monitoring of many retinal diseases. A high-fidelity retinal image is important for accurate screening, diagnosis, and monitoring. Bright illumination of the retina through the pupil improves image fidelity but often creates optical aberrations or image artifacts, such as corneal reflections, iris reflections, or lens flare, if the retinal camera and illumination source are not adequately aligned with the eye.

Accordingly, camera alignment is important, particularly with conventional retinal cameras, which typically have a very limited eyebox due to the need to block the deleterious image artifacts listed above. The eyebox for a retinal camera is a three-dimensional region in space typically defined relative to an eyepiece of the retinal camera and within which the center of a pupil or cornea of the eye should reside to acquire an acceptable image of the retina. The small size of conventional eyeboxes makes retinal camera alignment difficult and patient interactions during the alignment process often strained.

Various solutions have been proposed to alleviate the alignment problem. For example, moving/motorized stages that automatically adjust the retina-camera alignment have been proposed. However, these stages tend to be mechanically complex and substantially drive up the cost of a retinal imaging platform. An effective and low-cost solution for efficiently and easily achieving eyebox alignment of a retinal camera would improve the operation and accessibility of retinal cameras.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 3A is a perspective view of an eye cup, in accordance with an embodiment of the disclosure.

FIG. 3B is a plan view of the eye cup of FIG. 3A, in accordance with an embodiment of the disclosure.

FIG. 3C is a cross-section view of the eye cup of FIG. 3A, in accordance with an embodiment of the disclosure.

FIG. 7A is a perspective view of an eye cup, in accordance with an embodiment of the disclosure.

FIG. 7B is a plan view of the eye cup of FIG. 7A, in accordance with an embodiment of the disclosure.

FIG. 7C is a cross-section view of the eye cup of FIG. 7A, in accordance with an embodiment of the disclosure.

DETAILED DESCRIPTION

Embodiments of an eye cup and a retinal imaging system for aligning an eye with the retinal imaging system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
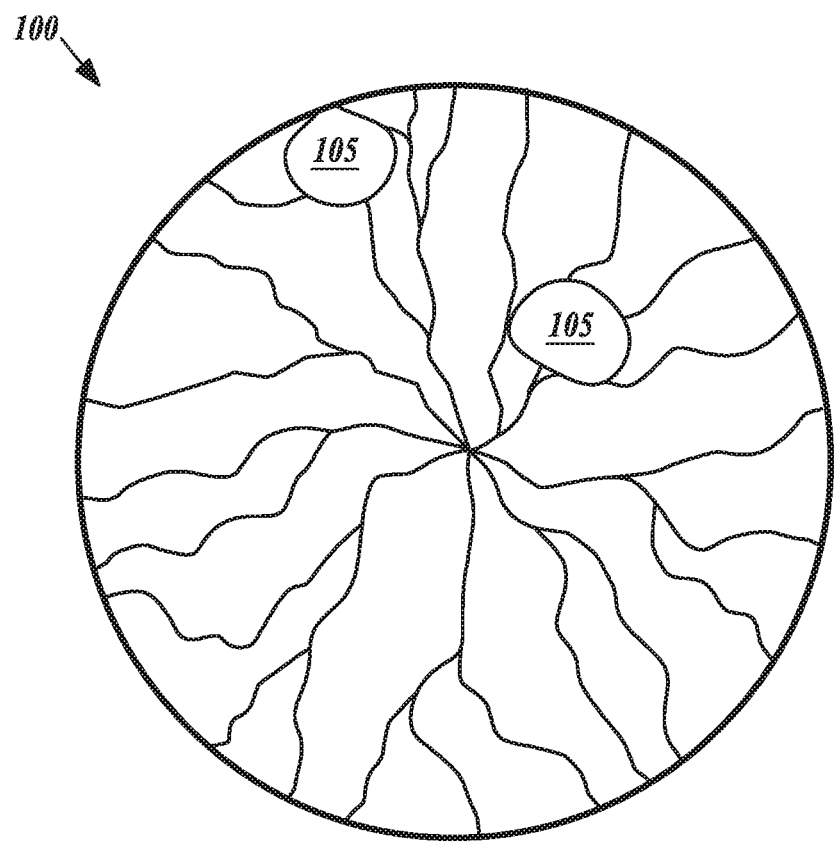
FIG. 1 illustrates a retinal image including a demonstrative image artifact due to misalignment of the retinal camera.

High-fidelity retinal images are important for screening, diagnosing, and monitoring many retinal diseases. To this end, reducing or eliminating instances of image artifacts that occlude, or otherwise malign, portions of the retinal image is desirable. FIG. 1 illustrates an example retinal image 100 with multiple image artifacts 105. These image artifacts 105 may arise when misalignment between the retinal imaging system and the eye permit stray light and deleterious reflections from the illumination source to enter the imaging path and ultimately are captured by the retinal image sensor with the image light.

To capture a retinal image, the lens tube (including the eyepiece lens) must be precisely aligned with a subject's eye (usually to a tolerance of just a few millimeters). In order to achieve this precise alignment, most retinal cameras include some sort of fixation target in the optical path that is visible when looking directly into the eyepiece lens. Among other purposes, the fixation target provides feedback about where to look during alignment. However, due to the optical properties of typical lens tubes, even just getting one's eye to the region in space where the fixation target is visible is often challenging. Without any feedback to facilitate a coarse alignment, a grossly misaligned user is often unsure how to move relative to the eyepiece lens to gain visual contact with the fixation target, at which point fine or precise alignment can begin using the fixation target.

Figure 2A:
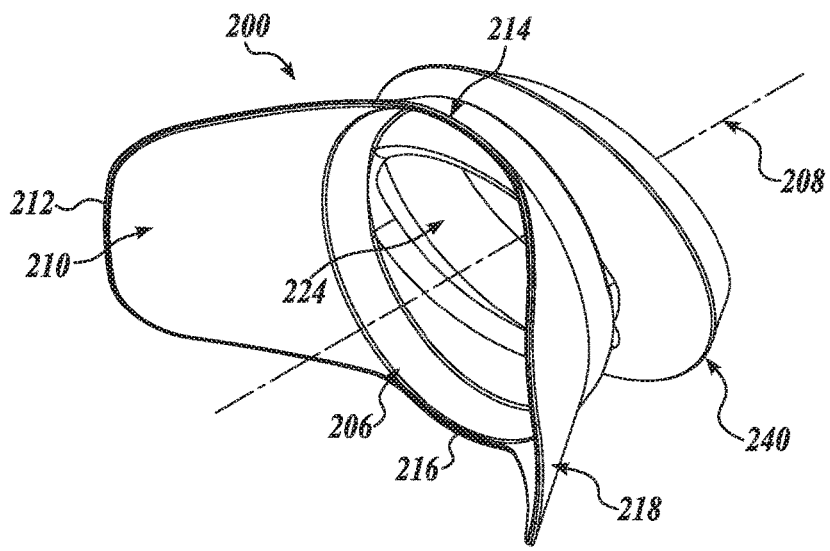
FIG. 2A is a perspective view of an eye cup, in accordance with an embodiment of the disclosure.
Figure 2B:
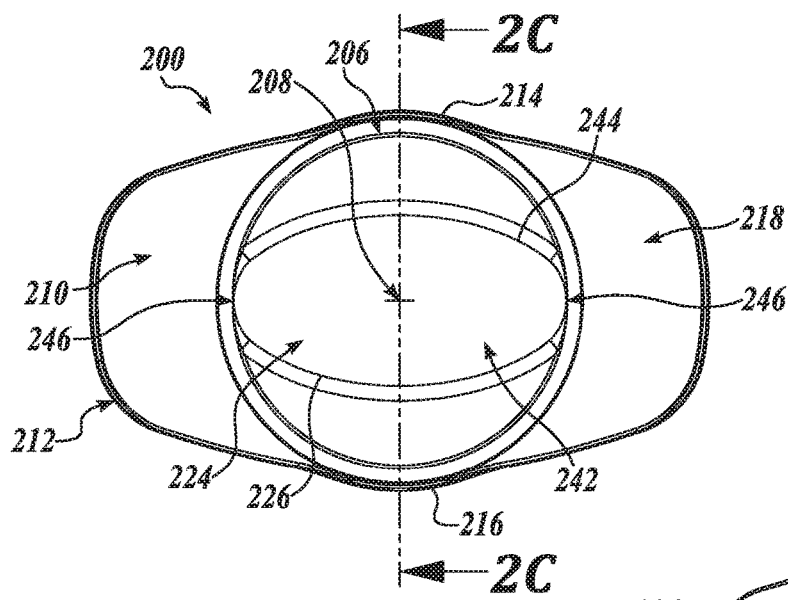
FIG. 2B is a plan view of the eye cup of FIG. 2A, in accordance with an embodiment of the disclosure.
Figure 2C:
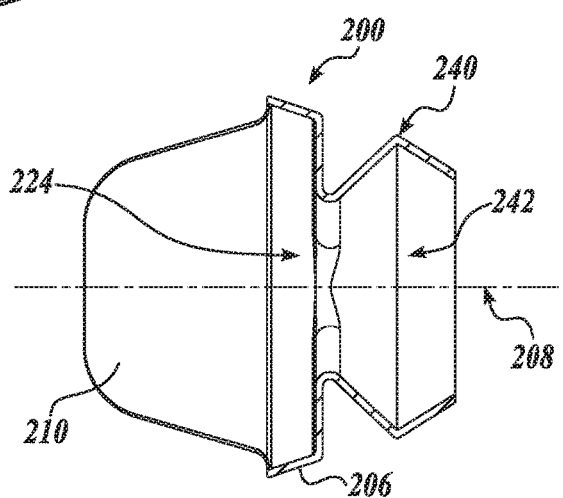
FIG. 2C is a cross-section view of the eye cup of FIG. 2A, in accordance with an embodiment of the disclosure.
Figure 2D:
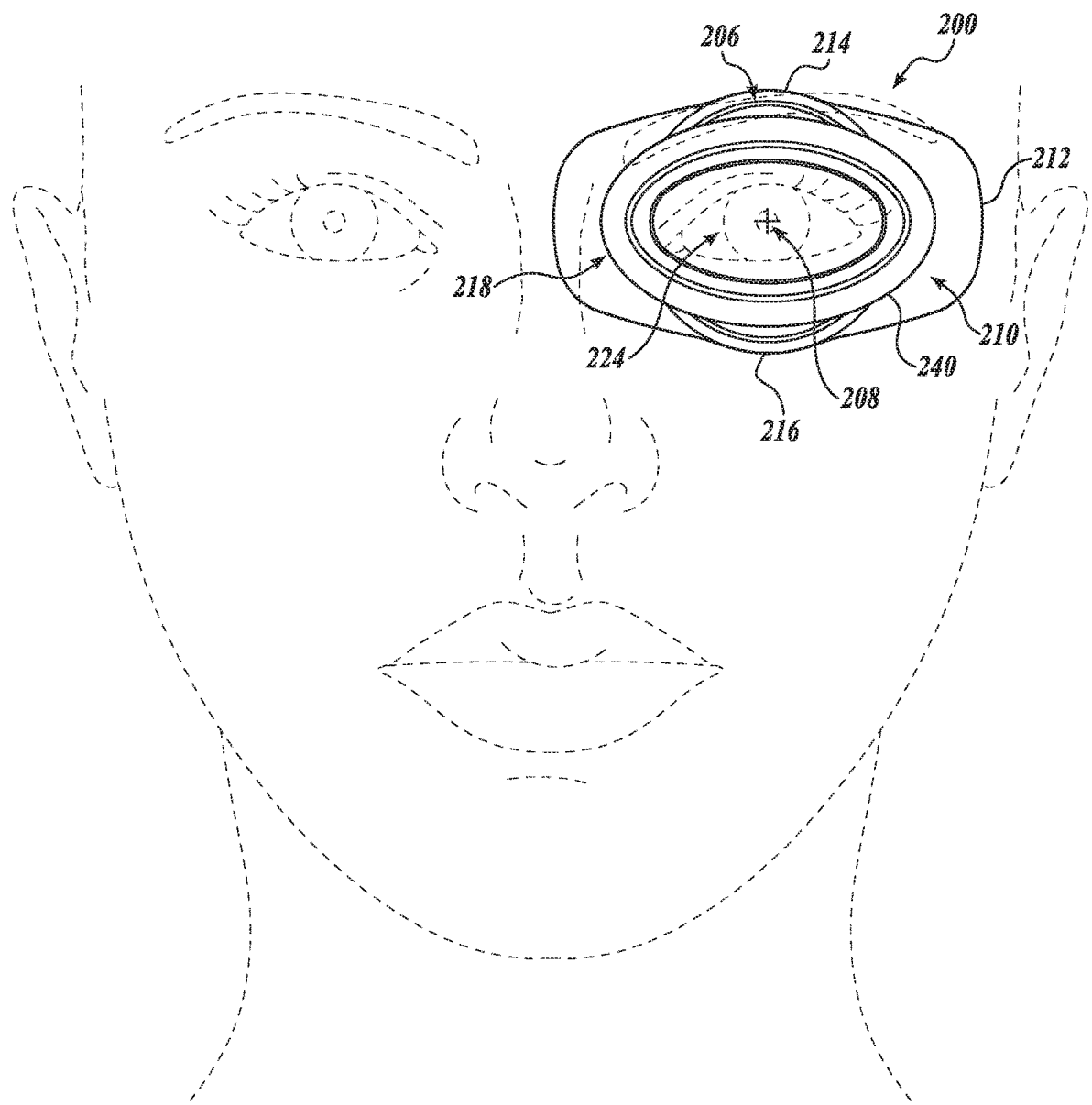
FIG. 2D is another plan view of the eye cup of FIG. 2A shown coupled to a periorbital region of an eye, in accordance with an embodiment of the disclosure.

In order to assist the end user or patient in attaining an initial (coarse) alignment with the eyepiece lens, embodiments disclosed herein use an eye cup configured to provide passive tactile feedback. The eye cup is configured to guide the user's eye into sufficient course alignment with the eyepiece lens such that the user can, for example, see the fixation target, which is then used for fine alignment in preparation for obtaining a high-fidelity retinal image. The fine alignment may be achieved via high precision retinal tracking through the eyepiece lens using the retinal image sensor itself Attention is directed to FIGS. 2A-2D in which an eye cup 200 shaped to couple with an eyepiece lens assembly, in accordance with an embodiment of the disclosure, is described. FIG. 2A is a perspective view of the eye cup 200. FIG. 2B is a plan view of the eye cup 200. FIG. 2C is a cross-section view of the eye cup 200. FIG. 2D is another plan view of the eye cup 200 shown coupled to a periorbital region of an eye.

As shown, the eye cup 200 includes a concave socket 206 shaped to define a viewing aperture 224 having a longitudinal axis 208, and a flange 210 extending from the concave socket 206 away from the longitudinal axis 208. As described further herein, the concave socket 206 is shaped to couple to a periorbital region of an eye. Likewise, the viewing aperture 224 is positioned about the concave socket 206 to align with a pupil of the eye along the longitudinal axis 208 of the viewing aperture 224 when the concave socket 206 is coupled to the periorbital region. In this regard, as a user couples their periorbital region to the concave socket 206, of a pupil of their eye is generally aligned along the longitudinal axis 208 of the viewing aperture 224 and, accordingly, an eyepiece lens assembly coupled to the eye cup 200.

In the illustrated embodiment, the flange 210 is shown shaped to couple with a lateral margin of the periorbital region when the concave socket 206 is coupled to the periorbital region. See, e.g., FIG. 2D. In an embodiment, the flange 210 and the concave socket 206 comprise a flexible material, such as a silicone rubber, configured to deform under pressure from a periorbital region. Additionally, in an embodiment, the flange 210 and the concave socket 206 are biased to resist pressure from the periorbital region. In this regard, the flange 210 and the concave socket 206 are configured to provide passive feedback, such as passive tactile feedback, to a user in aligning their periorbital region and, accordingly, their eye with the viewing aperture 224 and an eyepiece assembly coupled to the eye cup 200. In an embodiment, deformation of the eye cup 200, such as due to stretching, pulling, or flexing of the flexible material, provides a force that varies based on alignment of the eye cup 200. Such passive, tactile feedback is suitable to gently guide a user's eye into coarse alignment with an eyepiece lens assembly such that their retina is positioned within an eyebox of a retinal imaging camera.

As shown, an outer edge 212 of the flange 210 extends farther from the longitudinal axis 208 than an outer edge of portions 214 and 216 of the concave socket 206 positioned to couple with a supraorbital margin or an infraorbital margin of the periorbital region when the concave socket 206 is coupled to the periorbital region. See FIG. 2D. Humans tend to align their eyes better vertically (i.e. between cranial and caudal regions of their body) than they do between left and right portions of their eyes. In this regard, the flange 210 extends farther from the longitudinal axis 208 than other portions 214 and 216 of the eye cup 200 to provide a greater amount of lateral passive tactile feedback to provide greater assistance in eye alignment.

Additionally, in an embodiment, a spring constant of the flange 210 is greater than a spring constant of portions 214 and 216 of the concave socket 206 positioned to couple with a supraorbital margin or an infraorbital margin of the periorbital region when the concave socket 206 is coupled to the periorbital region. Such a difference in spring constants in also suitable to provide greater lateral tactile feedback to assist in eye alignment to compensate for the general human deficiency in lateral eye alignment. In an embodiment, the difference in spring constants between the flange 210 and the portions 214 and 216 of the concave socket 206 positioned to couple with a supraorbital margin or an infraorbital margin of the periorbital region is due, at least in part, to a difference in an amount of flexible material in each of the respective regions of the eye cup 200.

In the illustrated embodiment, the flange 210 is a first flange 210, and the eye cup 200 further includes a second flange 218 extending away from the longitudinal axis 208 opposite the first flange 210. As shown, the second flange 218 is shaped to couple a bridge of a nose when the concave socket 206 is coupled to the periorbital region. In this regard, the eye cup 200 is shaped to assist with lateral alignment of an eye in both left and right directions.

The eye cup 200 is also shown to include bellows 240. Such bellows 240 define a bellows aperture 242 overlapping with the viewing aperture 224. Alignment of the bellows aperture 242 with the viewing aperture 224 allows a user to see through the eye cup 200, such as through an eyepiece lens assembly coupled thereto and to a fixation target of a retinal imaging camera.

As shown, the bellows 240 are positioned opposite a portion of the concave socket 206 shaped to contact the periorbital region. The bellows 240 are shaped to compress along the longitudinal axis 208. In this regard, the bellows 240 are configured to assist in aligning a depth of the eye along or about the longitudinal axis 208 to place a retina of the eye within an eye box of a retinal imaging camera.

In an embodiment, the bellows 240 are also configured to flex about the longitudinal axis 208. As shown, a periphery 244 of the bellows aperture 242 defines an ovoid shape. In the illustrated embodiment, the bellows 240 are shaped such that apexes 246 of the bellows aperture 242 extend farther toward a portion of the eye cup 200 shaped to couple with the lateral margin of the periorbital region and a bridge of a nose than the portions 214 and 216 of the eye cup 200 positioned to couple with a supraorbital margin or an infraorbital margin of the periorbital region when the concave socket 206 is coupled to the periorbital region. In this regard, the bellows 240 are shaped to provide greater lateral tactile feedback as they flex and/or stretch laterally about the longitudinal axis 208 than tactile feedback due to vertical bellows 240 flex about longitudinal axis 208. As discussed further herein, greater lateral tactile feedback is suitable to compensate for person's generally decreased ability to laterally align their eyes.

FIGS. 3A-3C illustrate an eye cup 300, in accordance with an embodiment of the disclosure. FIG. 3A is a perspective view of the eye cup 300. FIG. 3B is a plan view of the eye cup 300. FIG. 3C is a cross-section view of the eye cup 300.

As shown, the eye cup 300 includes a concave socket 306 shaped to couple to a periorbital region of an eye, the concave socket 306 defining a viewing aperture 324 positioned to align with a pupil of the eye along a longitudinal axis 308 of the viewing aperture 324 when the concave socket 306 is coupled to the periorbital region; and a flange 310 extending from the concave socket 306 away from the longitudinal axis 308 and shaped to couple with a lateral margin of the periorbital region when the concave socket 306 is coupled to the periorbital region. The eye cup 300 is further shown to include a second flange 318 extending from the longitudinal axis 308 opposite the first flange 310. In an embodiment, the second flange 318 is shaped to couple a bridge of a nose when the concave socket 306 is coupled to the periorbital region.

In the illustrated embodiment, an outer edge 312 of the flange 310 extends farther from the longitudinal axis 308 than an outer edge of portions 314 and 316 of the concave socket 306 positioned to couple with a supraorbital margin or an infraorbital margin of the periorbital region when the concave socket 306 is coupled to the periorbital region. As discussed further herein with respect to FIGS. 2A-2D, such a configuration is suitable to aid in lateral alignment of an eye coupled to the eye cup 300.

The eye cup 300 is also shown to include bellows 340 positioned opposite a portion of the concave socket 306 shaped to contact the periorbital region and defining a bellows aperture 342 overlapping with the viewing aperture 324. In an embodiment, the bellows 340 are shaped to compress along the longitudinal axis 308. As shown, a periphery 344 of the bellows aperture 342 defines an ovoid shape, wherein apexes 346 of the bellows aperture 342 extend farther toward a portion of the eye cup 300 shaped to couple with the lateral margin of the periorbital region and a bridge of a nose than the portions 314 and 316 of the eye cup 300 positioned to couple with a supraorbital margin or an infraorbital margin of the periorbital region when the concave socket 306 is coupled to the periorbital region.

In the illustrated embodiment, the eye cup 300 further includes an eyepiece lens assembly socket 334 shaped to couple with an eyepiece lens assembly, such as an eyepiece lens assembly of a retinal imaging camera. As shown, the eyepiece lens assembly socket 334 is positioned opposite a portion of the concave socket 306 shaped to couple with the periorbital region. In this regard, the eye cup 300 is shaped to be placed in between a periorbital region of a user and an eyepiece lens assembly to assist in alignment between the periorbital region and the eyepiece lens assembly.

The eyepiece lens assembly socket 334 is shown to define a first slot 336. In an embodiment, the first slot 336 is shaped to accept an alignment tracking camera of a retinal imaging camera. As discussed further herein with respect to FIGS. 8A and 8B, such an alignment tracking camera is suitable to assist with fine alignment of the eye and image sensor. In the illustrated embodiment, the first slot 336 is positioned adjacent to an apex 346 of the periphery 344 of the bellows aperture 342.

The eyepiece lens assembly socket 334 is shown to further define second slot 338 shaped to accept a second alignment tracking camera, the second slot 338 positioned opposite the first slot 336 and adjacent to another apex 346 of the periphery 344 of the bellows aperture 342, such as for coupling to an eyepiece lens assembly or retinal imaging camera including two opposing retinal imaging cameras. While the first and second slots 336 and 338 are shown positioned adjacent to apexes 346 of the bellows aperture 342, such as centered vertically about the eyepiece lens assembly socket 334, other configurations, such as in which the first and second slots 336 and 338 are not vertically centered, are within the scope of the present disclosure.

Figure 4A:
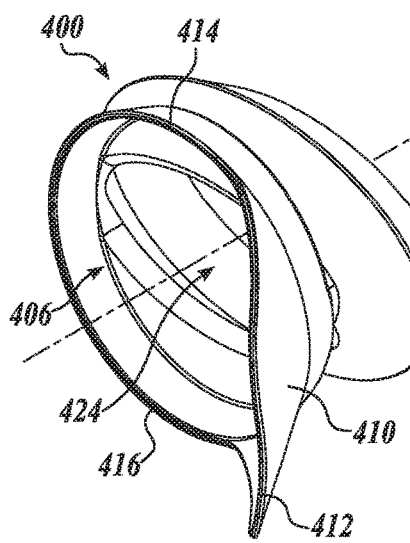
FIG. 4A is a perspective view of an eye cup, in accordance with an embodiment of the disclosure.
Figure 4B:
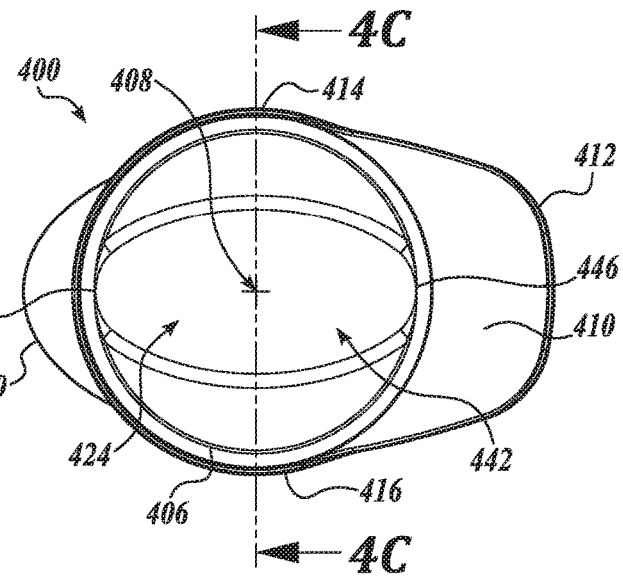
FIG. 4B is a plan view of the eye cup of FIG. 4A, in accordance with an embodiment of the disclosure.
Figure 4C:
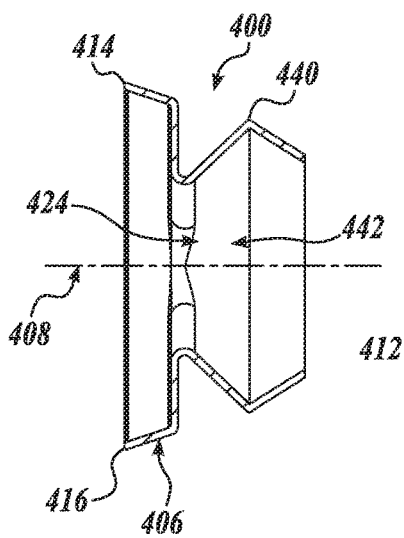
FIG. 4C is a cross-section view of the eye cup of FIG. 4A, in accordance with an embodiment of the disclosure.
Figure 4D:
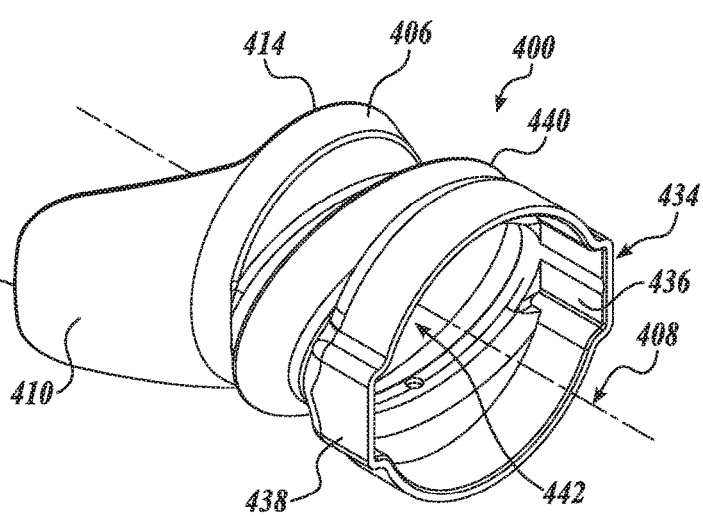
FIG. 4D is another perspective view of the eye cup of FIG. 4A shown including an eyepiece lens assembly socket, in accordance with an embodiment of the disclosure.

FIGS. 4A-4D illustrate another eye cup 400, in accordance with an embodiment of the disclosure. FIG. 4A is a perspective view of the eye cup 400. FIG. 4B is a plan view of the eye cup 400. FIG. 4C is a cross-section view of the eye cup 400. FIG. 4D is another perspective view of the eye cup 400.

The eye cup 400 is shown to include a concave socket 406 shaped to couple to a periorbital region of an eye, the concave socket 406 defining a viewing aperture 424 positioned to align with a pupil of the eye along a longitudinal axis 408 of the viewing aperture 424 when the concave socket 406 is coupled to the periorbital region; and a flange 410 extending from the concave socket 406 away from the longitudinal axis 408 and shaped to couple with a lateral margin of the periorbital region when the concave socket 406 is coupled to the periorbital region. As shown, an outer edge 412 of the flange 410 extends farther from the longitudinal axis 408 than an outer edge of portions 414 and 416 of the concave socket 406 positioned to couple with a supraorbital margin or an infraorbital margin of the periorbital region when the concave socket 406 is coupled to the periorbital region.

The eye cup 400 is also shown to include bellows 440 defining a bellows aperture 442 having apexes 446 and an eyepiece lens assembly socket 434 defining slots 436 and 438 as discussed further herein with respect to FIGS. 2A-2D and 3A-3C.

The eye cup 400 is shown to include a single flange 410. Rather, a portion of the eye cup 400 opposite the flange 410 defines an outer edge of the concave socket 406. In this regard, the eye cup 400 is shaped to provide increased lateral tactile feedback, such as to a lateral margin of a periorbital region, to a user in a single direction rather than in both left and right directions. Such a configuration may be suitable, for example, where the eye cup 400 can be rotated about the longitudinal axis 408 when switching between eyes, or where only a single eye is being examined.

Figure 5A:
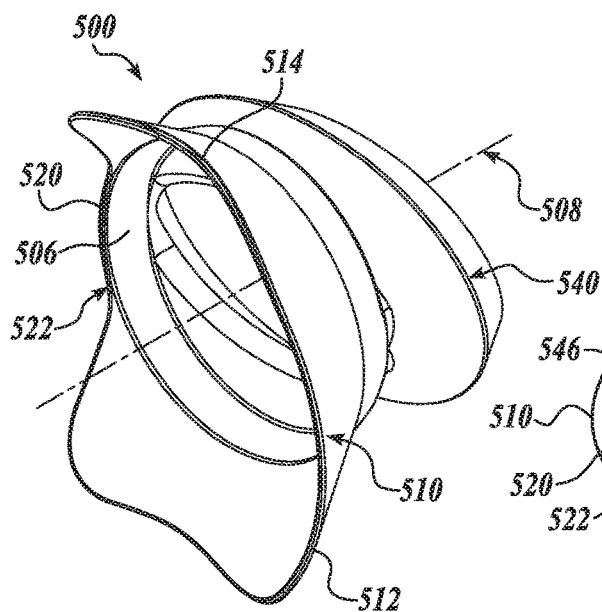
FIG. 5A is a perspective view of an eye cup, in accordance with an embodiment of the disclosure.
Figure 5B:
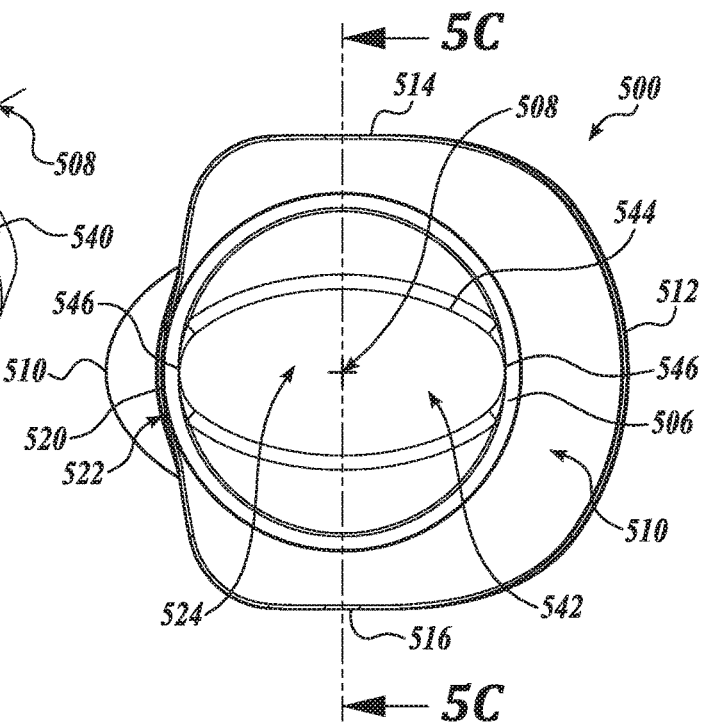
FIG. 5B is a plan view of the eye cup of FIG. 5A, in accordance with an embodiment of the disclosure.
Figure 5C:
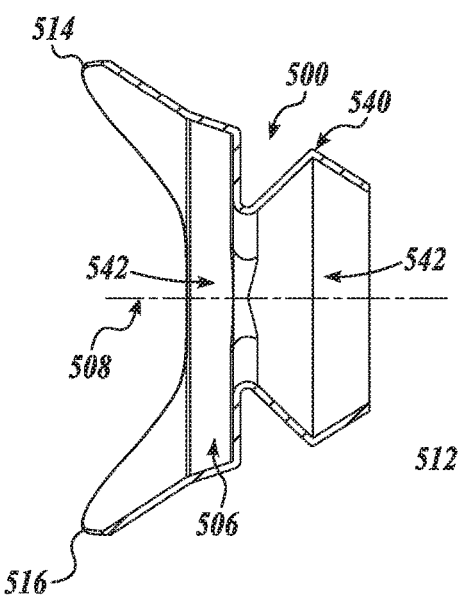
FIG. 5C is a cross-section view of the eye cup of FIG. 5A, in accordance with an embodiment of the disclosure.
Figure 5D:
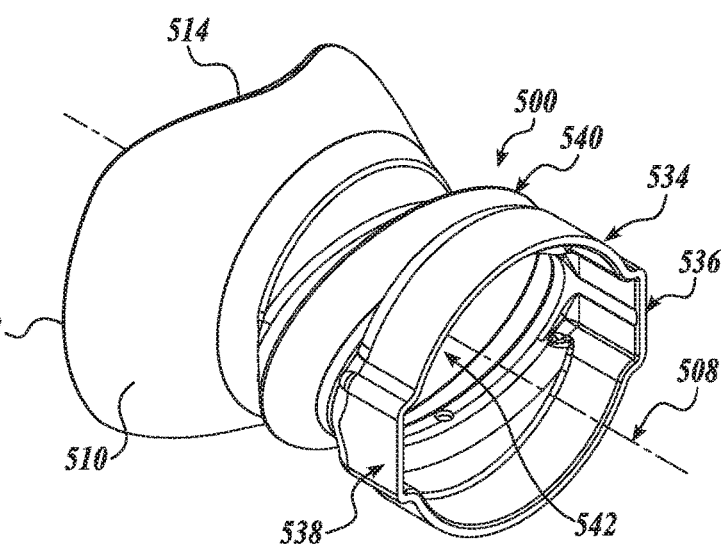
FIG. 5D is another perspective view of the eye cup of FIG. 5A shown including an eyepiece lens assembly socket, in accordance with an embodiment of the disclosure.

FIGS. 5A-5D illustrate an eye cup 500 shaped to couple with an eyepiece lens assembly, in accordance with an embodiment of the disclosure. FIG. 5A is a perspective view of the eye cup 500. FIG. 5B is a plan view of the eye cup 500. FIG. 5C is a cross-section view of the eye cup 500. FIG. 5D is another perspective view of the eye cup 500.

As shown, the eye cup 500 includes a concave socket 506 shaped to couple to a periorbital region of an eye, the concave socket 506 defining a viewing aperture 524 positioned to align with a pupil of the eye along a longitudinal axis 508 of the viewing aperture 524 when the concave socket 506 is coupled to the periorbital region; and a flange 510 extending from the concave socket 506 away from the longitudinal axis 508 and shaped to couple with a lateral margin of the periorbital region when the concave socket 506 is coupled to the periorbital region.

The eye cup 500 is also shown to include bellows 540 defining a bellows aperture 542 having apexes 546 and an eyepiece lens assembly socket 534 defining slots 536 and 538 as discussed further herein with respect to FIGS. 2A-2D and 3A-3C.

As shown, the eye cup 500 is shown to define a single flange 510 disposed on a lateral side of the eye cup 500 positioned to couple with a lateral margin of a periorbital region of an eye. An edge 520 of the concave socket 506 positioned opposite the flange 510 defines a contour 522 shaped to abut a bridge of a nose of when the concave socket 506 is coupled to the periorbital region. In this regard, the eye cup 500 is shaped to provide lateral tactile feedback to a user in aligning their eye with an eye piece lens assembly coupled to the eye cup 500 and shaped to comfortably accommodate the bridge of their nose while the eye cup 500 is coupled to their periorbital region.

The eye cup 500 is shown to further define extensions of the concave socket 506 shaped and positioned to couple with a supraorbital margin or an infraorbital margin of the periorbital region when the concave socket 506 is coupled to the periorbital region. However, an outer edge 512 of the flange 510 extends farther from the longitudinal axis 508 than an outer edge of the portions 514 and 516 of the concave socket 506 positioned to couple with the supraorbital margin or the infraorbital margin of the periorbital region when the concave socket 506 is coupled to the periorbital region. As discussed further herein, by having the flange 510 extend farther from the longitudinal axis 508 than other portions of the eye cup 500, such as portions 514 and 516, the flange 510 is configured to provide additional or more tactile feedback for vertically aligning the eye relative to an eyepiece lens assembly and/or retinal imaging camera.

Figure 6A:
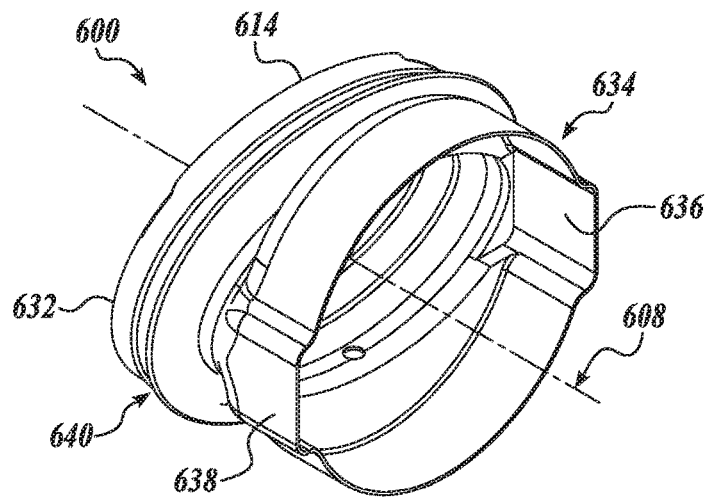
FIG. 6A is a perspective view of an eye cup, in accordance with an embodiment of the disclosure.
Figure 6B:
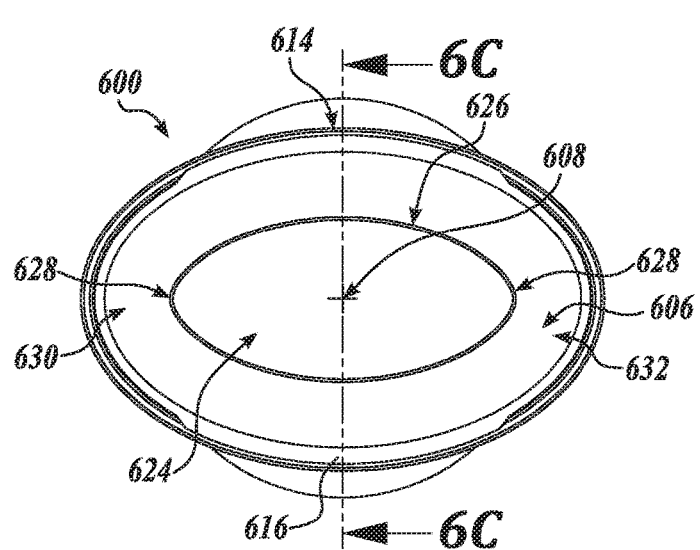
FIG. 6B is a plan view of the eye cup of FIG. 6A, in accordance with an embodiment of the disclosure.
Figure 6C:
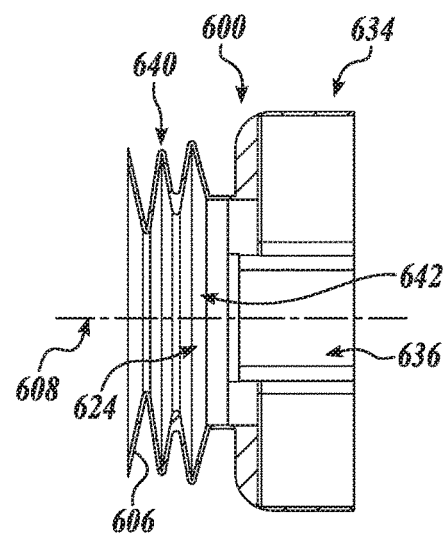
FIG. 6C is a cross-section view of the eye cup of FIG. 6A, in accordance with an embodiment of the disclosure.

FIGS. 6A-6C illustrate another eye cup 600, in accordance with an embodiment of the disclosure. FIG. 6A is perspective view of the eye cup 600. FIG. 6B is a plan view of the eye cup 600. FIG. 6C is cross-section view of the eye cup 600.

As shown, the eye cup 600 includes a concave socket 606 shaped to couple to a periorbital region of an eye, the concave socket 606 defining a viewing aperture 624 positioned to align with a pupil of the eye along a longitudinal axis 608 of the viewing aperture 624 when the concave socket 606 is coupled to the periorbital region. The eye cup 600 further includes an eyepiece lens assembly socket 634 positioned opposite a portion of the concave socket 606 shaped to couple with the periorbital region, the eyepiece lens assembly socket 634 shaped to couple with an eyepiece lens assembly. As shown, the eyepiece lens assembly socket 634 defines opposing first and second slots 636 and 638 shaped to accept alignment tracking cameras. In the illustrated embodiment, the eye cup 600 includes bellows 640 positioned opposite a portion of the concave socket 606 shaped to contact the periorbital region and configured to compress along the longitudinal axis 608. As shown, the eyepiece lens assembly socket 634 defines a bellows aperture 642 overlapping with the viewing aperture 624.

As shown, an outer edge of the concave socket 606 defines an ovoid shape. Likewise, a periphery 626 of the viewing aperture 624 defines an ovoid shape corresponding to or in registry with the ovoid shape of the outer edge of the concave socket 606. In the illustrated embodiment, apexes 628 of the periphery 626 of the viewing aperture 624 extend farther toward a portion of the eye cup 600 shaped to couple with the lateral margin of the periorbital region and a bridge of a nose than portions 614 and 616 of the eye cup 600 shaped to couple with a supraorbital margin or an infraorbital margin. Such an ovoid shape the concave socket 606 is suitable to provide a greater amount of tactile feedback laterally than vertically as discussed further herein, for example, with respect to the flanges 210 and 218 of FIGS. 2A-2D.

FIGS. 7A-7C illustrate an eye cup 700, in accordance with an embodiment of the disclosure. FIG. 7A is a perspective view of the eye cup 700. FIG. 7B is a plan view of the eye cup 700. FIG. 7C is a cross-section view of the eye cup 700.

As shown, the eye cup 700 includes a concave socket 706 shaped to couple to a periorbital region of an eye, the concave socket 706 defining a viewing aperture 724 positioned to align with a pupil of the eye along a longitudinal axis 708 of the viewing aperture 724 when the concave socket 706 is coupled to the periorbital region. The eye cup 700 further includes an eyepiece lens assembly socket 734 positioned opposite a portion of the concave socket 706, the eyepiece lens assembly socket 734 shaped to couple with the periorbital region and shaped to couple with an eyepiece lens assembly. As shown, the eye cup 702 defines opposing first and second slots 736 and 738 shaped to accept alignment tracking cameras. In the illustrated embodiment, the eye cup 700 includes bellows 740 positioned opposite a portion of the concave socket 706 shaped to contact the periorbital region, the bellows 740 configured to compress along the longitudinal axis 708. As shown, the bellows 740 define a bellows aperture 742 overlapping with the viewing aperture 724.

In the illustrated embodiment, an outer edge 720 of the concave socket 706 is rotationally symmetric about the longitudinal axis 708. In this regard, the outer edge 720 of the concave socket 706 encircles the longitudinal axis 708.

As above, the eye cup 700 includes bellows 740. As shown, a periphery 744 of the bellows aperture 742 defines an ovoid shape. Apexes 746 of the bellows aperture 742 extend farther toward a portion of the eye cup 700 shaped to couple with the lateral margin of the periorbital region and a bridge of a nose than the portions of the eye cup 700 positioned to couple with a supraorbital margin or an infraorbital margin of the periorbital region when the concave socket 706 is coupled to the periorbital region. As discussed further herein with respect to FIGS. 3A-3C, such ovoid bellows 740 are configured to provide greater amounts of tactile feedback when deformed in a direction toward lateral margins of a periorbital region of an eye than for deformations in a direction toward either the supraorbital margin or the infraorbital margin of the periorbital region. As also discussed further herein, such deformation characteristics are suitable to guide coarse alignment of an eye with a retinal imaging camera and compensate for a person's lesser ability to laterally an eye.

Figure 8A:
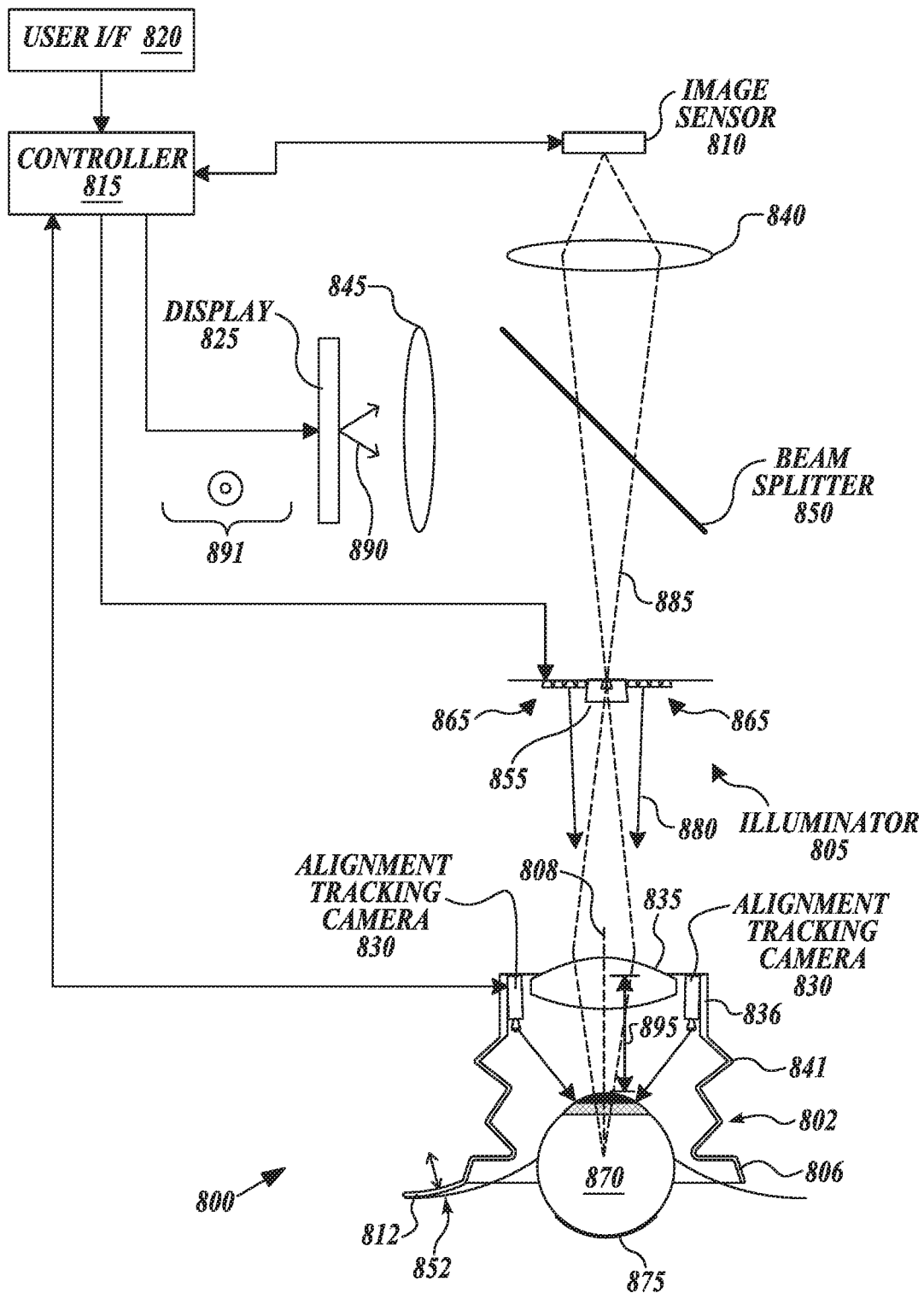
FIG. 8A is a functional component diagram illustrating a retinal imaging system with an eye cup for coarse alignment, in accordance with an embodiment of the disclosure.
Figure 8B:
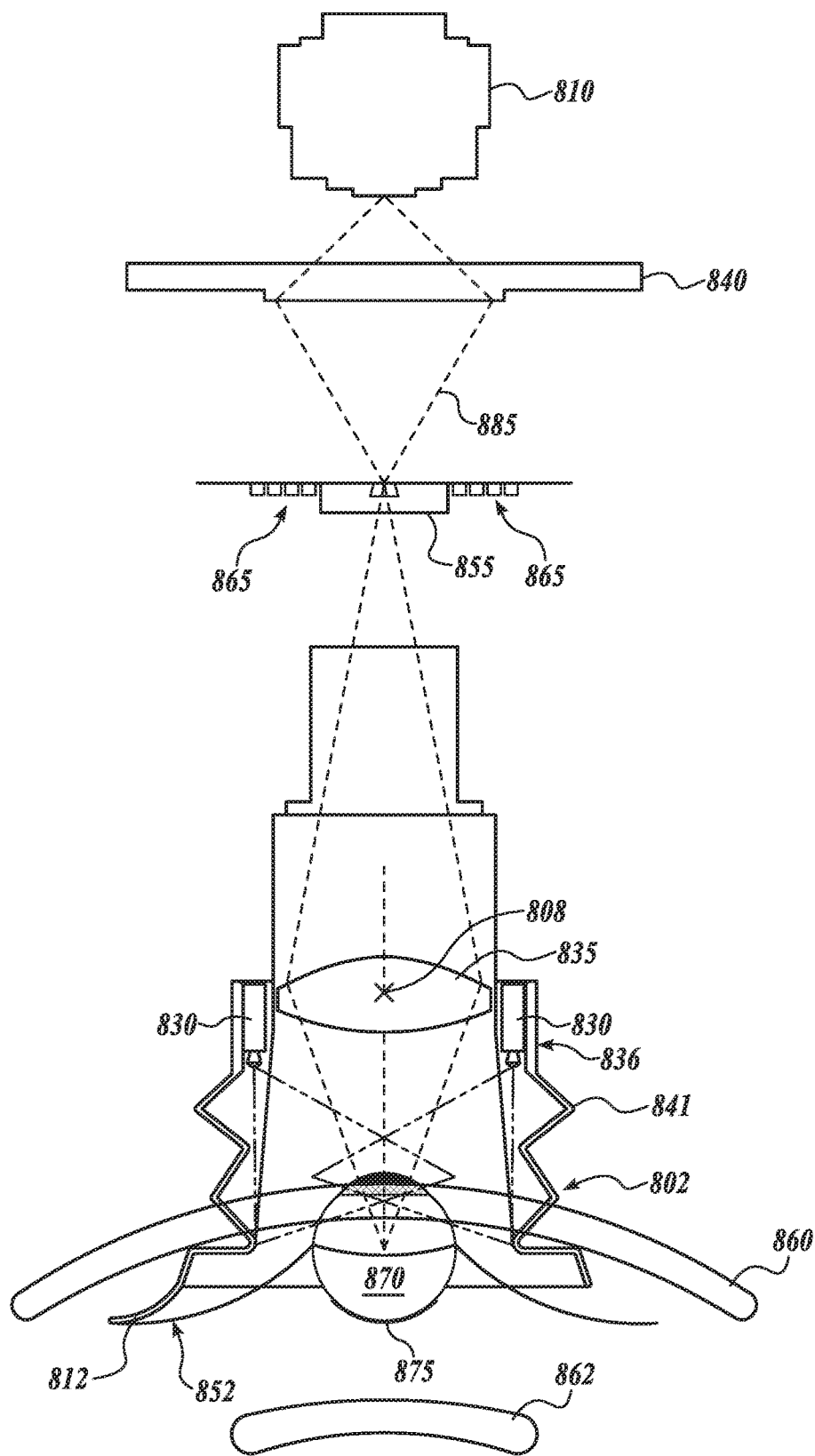
FIG. 8B is a functional component diagram illustration a portion of the retinal imaging system of FIG. 8A, in accordance with an embodiment of the disclosure.

FIG. 8A is a functional component diagram illustrating a retinal imaging system 800 with an eye cup 802 for coarse alignment, in accordance with an embodiment of the disclosure. FIG. 8B is a functional component diagram illustration a portion of the retinal imaging system. The illustrated embodiment of retinal imaging system 800 includes an eye cup 802, an illuminator 805, an image sensor 810 (also referred to as a retinal image sensor), a controller 815, a user interface 820, a display 825, alignment tracking camera(s) 830, and an optical relay system. The illustrated embodiment of the optical relay system includes lens assemblies 835, 840, 845 and a beam splitter 850. The illustrated embodiment of illuminator 805 comprises illuminator arrays 865 and a center aperture 855. The illustrated embodiment is shown to include an eye cup 802.

The optical relay system serves to direct (e.g., pass or reflect) illumination light 880 output from illuminator 805 along an illumination path through the pupil of eye 870 to illuminate retina 875 while also directing image light 885 of retina 875 (i.e., the retinal image) along an imaging path to image sensor 810. Image light 885 is formed by the scattered reflection of illumination light 880 off of retina 875. In the illustrated embodiment, the optical relay system further includes beam splitter 850, which passes at least a portion of image light 885 to image sensor 810 while also optically coupling fixation target 891 to eyepiece lens assembly 835 and directing display light 890 output from display 825 to eye 870. Beam splitter 850 may be implemented as a polarized beam splitter, a non-polarized beam splitter (e.g., 90% transmissive and 10% reflective, 50/50 beam splitter, etc.), a dichroic beam splitter, or otherwise. The optical relay system includes a number of lenses, such as lenses 835, 840, and 845, to focus the various light paths as needed. For example, lens 835 may include one or more lensing elements that collectively form an eyepiece lens assembly 835 that is housed within a lens tube (not illustrated in FIGS. 8A and 8B). The eyepiece lens is displaced from the cornea of eye 870 by an eye relief 895 during operation. Lens 840 may include one or more lens elements for bringing image light 885 to a focus on image sensor 810. Lens 845 may include one or more lens elements for focusing display light 890. It should be appreciated that optical relay system may be implemented with a number and variety of optical elements (e.g., refractive lenses, reflective surfaces, diffractive surfaces, etc.) and may vary from the configuration illustrated in FIGS. 8A and 8B.

In one embodiment, display light 890 output from display 825 represents a fixation target. The fixation target may be an image of a plus-sign, a bullseye, a cross, a target, or other shape (e.g., see demonstrative fixation target images 891). The fixation target not only can aid with obtaining fine or precise alignment between eyepiece lens 835 and eye 870 by providing visual feedback to the patient, but also gives the patient a fixation target upon which to accommodate and stabilize their vision. Display 825 may be implemented with a variety of technologies including a liquid crystal display (LCD), light emitting diodes (LEDs), various illuminated shapes (e.g., an illuminated cross or concentric circles), or otherwise. Of course, the fixation target may be implemented in other manners than a virtual image on a display. For example, the fixation target may be a physical object (e.g., crosshairs, etc.).

The illustrated embodiment of eye cup 802 is shown to include bellows 841, a concave socket 806 shaped to couple with the periorbital region of the eye 801. As shown, the eye cup 802 defines a viewing aperture 824 about a longitudinal axis 808 generally in line with the optical relay. The eye cup 802 is also shown to include a flange 812 extending away from the longitudinal axis 808 and shaped to couple with the periorbital region 852. As discussed further herein with respect, for example, to FIGS. 2A-2D, such a flange 812 is configured to provide passive tactile feedback to a user in coarse alignment of the eye 870 with the eyepiece lens assembly 835, such as coarse lateral alignment.

The eye cup 802 is also shown to include an eyepiece lens assembly socket 836 coupled to the eyepiece lens assembly 835. In the illustrated embodiment, the eyepiece lens assembly socket 836 is shown to accommodate alignment tracking cameras 836, as discussed further herein with respect to FIGS. 3A-3C.

In the illustrated embodiment, the retinal camera system 800 is shown to include a headrest 860. As shown, the head rest 860 is positioned to contact a forehead of a user when the eye cup 802 is coupled to the periorbital region 850.

The head rest 860 is shown to define a curvature shaped to couple to temples of the user. Such a headrest curvature is suitable to provide additional lateral tactile feedback in addition to lateral passive tactile feedback provided, for example, by the flange 812 of the eye cup 802. In an embodiment, the retinal imaging system 800 alternatively or additionally includes a chin rest 862 positioned to contact a chin of a user when the eye cup 802 is coupled to the periorbital region. In an embodiment, the chin rest 862 defines a curvature shaped to provide additional lateral tactile feedback in addition to lateral passive tactile feedback provided, for example, by the flange 812 of the eye cup 802.

Image sensor 810 may be implemented using a variety of imaging technologies, such as complementary metal-oxide-semiconductor (CMOS) image sensors, charged-coupled device (CCD) image sensors, or otherwise. In one embodiment, image sensor 810 includes an onboard memory buffer or attached memory to store/buffer retinal images.

Alignment tracking camera(s) 830 operate to track lateral and eye relief offset alignment (or misalignment) between retinal imaging system 800 and eye 870, and in particular, between eyepiece lens assembly 835 and eye 870. Alignment tracking camera 830 may operate using a variety of different techniques to track the relative position of eye 870 to retinal imaging system 800 including pupil tracking, iris tracking, or otherwise. In the illustrated embodiment, alignment tracking camera 830 includes two cameras disposed on either side of eyepiece lens assembly 835 to enable triangulation and obtain X, Y, and Z position information about the pupil or iris. In one embodiment, alignment tracking camera 830 includes one or more infrared (IR) emitters to track eye 870 via IR light while retinal images are acquired with visible spectrum light, and in some cases, with IR light as well.

Eye position, including lateral alignment and/or eye relief offset alignment, may be measured and tracked using retinal images acquired by image sensor 810 for precise alignment tracking, or separately/additionally, by alignment tracking camera(s) 830. Alignment tracking camera(s) 830 provide coarse alignment tracking via the pupil or iris. In the illustrated embodiment, alignment tracking camera(s) 830 are positioned externally to view eye 870 from outside of eyepiece lens assembly 835. In other embodiments, alignment tracking camera(s) 830 may be optically coupled via the optical relay components to view and track eye 870 through eyepiece lens assembly 835.

Controller 815 is coupled to image sensor 810, display 825, illuminator 805, alignment tracking camera 830, and visual guidance indicator 801 to choreograph their operation. Controller 815 may include software/firmware logic executing on a microcontroller, hardware logic (e.g., application specific integrated circuit, field programmable gate array, etc.), or a combination of software and hardware logic. Although FIG. 8A illustrates controller 815 as a distinct functional element, the logical functions performed by controller 815 may be decentralized across a number hardware elements. Controller 815 may further include input/output (I/O ports), communication systems, or otherwise. Controller 815 is coupled to user interface 820 to receive user input and provide user control over retinal imaging system 800. User interface 880 may include one or more buttons, dials, feedback displays, indicator lights, etc.

During operation, controller 815 operates illuminator 805 and retinal image sensor 810 to capture one or more retinal images. Illumination light 880 is directed through the pupil of eye 870 to illuminate retina 875. The scattered reflections from retina 875 are directed back along the image path through aperture 855 to image sensor 810. When eye 870 is properly aligned within the eyebox of system 800, aperture 855 operates to block deleterious reflections and light scattering that would otherwise malign the retinal image while passing the image light itself. Prior to capturing the retinal image, controller 815 operates visual guidance indicator 801 and alignment tracking camera(s) 830 to provide real-time visual feedback (i.e., visual cue 811) to eye 870 to achieve coarse alignment, at which point the user can see the fixation target. Controller 815 further operates display 825 to output a fixation target image 891 to guide the patient's gaze into fine or precise alignment. Once fine alignment is achieved, controller 815 deems eye 870 to be within the eyebox of retinal imaging system 800, and thus acquires a retinal image with image sensor 810.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye cup shaped to couple with an eyepiece lens assembly, the eye cup comprising:
   a concave socket shaped to couple to a periorbital region of an eye, the concave socket defining a viewing aperture positioned to align with a pupil of the eye along a longitudinal axis of the viewing aperture when the concave socket is coupled to the periorbital region; and
   a flange extending from the concave socket away from the longitudinal axis and shaped to couple with a lateral margin of the periorbital region when the concave socket is coupled to the periorbital region,
   wherein the flange has a greater spring constant than that of portions of the concave socket positioned to press against a supraorbital margin or an infraorbital margin of the periorbital region when the concave socket is pressed to the periorbital region.

2. The eye cup of claim 1, wherein an outer edge of the flange extends farther from the longitudinal axis than an outer edge of portions of the concave socket positioned to couple with a supraorbital margin or an infraorbital margin of the periorbital region when the concave socket is coupled to the periorbital region.

3. The eye cup of claim 1, wherein the flange is a first flange, the eye cup further comprising a second flange extending from the longitudinal axis opposite the first flange, wherein the second flange is shaped to couple a bridge of a nose when the concave socket is coupled to the periorbital region.

4. The eye cup of claim 1, wherein an edge of the concave socket positioned opposite the flange defines a contour shaped to abut a bridge of a nose when the concave socket is coupled to the periorbital region.

5. The eye cup of claim 1, wherein the flange and the concave socket comprise a flexible material configured to deform under pressure from a periorbital region, and wherein the flange and the concave socket are biased to resist pressure from the periorbital region.

6. The eye cup of claim 1, wherein a periphery of the viewing aperture defines an ovoid shape, wherein apexes of the periphery of the viewing aperture extend farther toward a portion of the eye cup shaped to couple with the lateral margin of the periorbital region and a bridge of a nose than portions of the eye cup shaped to couple with a supraorbital margin or an infraorbital margin.

7. The eye cup of claim 6, further comprising an eyepiece lens assembly socket positioned opposite a portion of the concave socket shaped to couple with the periorbital region and shaped to couple with an eyepiece lens assembly.

8. The eye cup of claim 7, wherein the eyepiece lens assembly socket defines a first slot positioned adjacent to an apex of the periphery of the viewing aperture and shaped to accept an alignment tracking camera of a retinal imaging camera.

9. The eye cup of claim 8, wherein the eyepiece lens assembly socket defines a second slot shaped to accept a second alignment tracking camera, the second slot positioned opposite the first slot and adjacent to another apex of the periphery of the viewing aperture.

10. The eye cup of claim 1, further comprising bellows defining a bellows aperture overlapping with the viewing aperture.

11. The eye cup of claim 10, wherein the bellows are positioned opposite a portion of the concave socket shaped to contact the periorbital region.

12. The eye cup of claim 10, wherein the bellows are shaped to compress along the longitudinal axis.

13. The eye cup of claim 10, wherein a periphery of the bellows aperture defines an ovoid shape, wherein apexes of the bellows aperture extend farther toward a portion of the eye cup shaped to couple with the lateral margin of the periorbital region and a bridge of a nose than the portions of the eye cup positioned to couple with a supraorbital margin or an infraorbital margin of the periorbital region when the concave socket is coupled to the periorbital region.

14. The eye cup of claim 1, wherein the concave socket and the flange are both formed of a flexible material and the concave socket extends at a different angle relative to the longitudinal axis than the flange.

15. A retinal camera system comprising:
an eyepiece lens assembly;
an eye cup comprising:
  a concave socket shaped to couple to a periorbital region of an eye, the concave socket defining a viewing aperture positioned to align with a pupil of the eye along a longitudinal axis of the viewing aperture when the concave socket is coupled to the periorbital region;
  a flange extending from the concave socket away from the longitudinal axis and shaped to couple with a lateral margin of the periorbital region when the concave socket is coupled to the periorbital region, wherein the flange has a greater spring constant than that of portions of the concave socket positioned to press against a supraorbital margin or an infraorbital margin of the periorbital region when the concave socket is pressed to the periorbital region; and
  an eyepiece lens assembly socket coupled with the eyepiece lens assembly; and
a retinal image sensor optically coupled to the eyepiece lens assembly positioned to acquire a retinal image of an eye through the eyepiece lens assembly and the eye cup.

16. The retinal imaging system of claim 15, wherein an outer edge of the flange extends farther from the longitudinal axis than an outer edge of portions of the concave socket positioned to couple with a supraorbital margin or an infraorbital margin of the periorbital region when the concave socket is coupled to the periorbital region.

17. The retinal imaging system of claim 15, wherein the flange and the concave socket are biased to resist pressure from the periorbital region of the user.

18. The retinal imaging system of claim 15, further comprising bellows defining a bellows aperture overlapping with the viewing aperture, wherein the bellows are coupled to the concave socket and shaped to compress along the longitudinal axis.

19. The retinal imaging system of claim 15, further comprising a chin rest positioned to contact a chin of a user when the eye cup is coupled to the periorbital region.

20. The retinal imaging system of claim 15, further comprising a headrest positioned to contact a forehead of a user when the eye cup is coupled to the periorbital region, wherein the headrest defines a curvature shaped to couple to temples of the user.

* * * * *